United States Patent [19]

Mecca

[11] 3,954,989
[45] May 4, 1976

[54] TOPICAL COMPOSITIONS CONTAINING AN ALLANTOIN ASCORBIC ACID COMPLEX
[75] Inventor: Sebastian B. Mecca, Abington, Pa.
[73] Assignee: Schuylkill Chemical Company, Philadelphia, Pa.
[22] Filed: Feb. 10, 1975
[21] Appl. No.: 548,198

Related U.S. Application Data
[62] Division of Ser. No. 462,779, April 22, 1974, Pat. No. 3,898,243.

[52] U.S. Cl.................................. 424/273; 424/43; 424/59; 424/68; 424/280
[51] Int. Cl.² ............... A61K 31/365; A61K 31/415
[58] Field of Search...................... 424/273, 280, 59

[56] References Cited
UNITED STATES PATENTS
2,376,884  5/1945  Schwenk et al....................... 424/59
2,761,867  9/1956  Mecca ............................ 424/273 X

OTHER PUBLICATIONS

Kirk – Othmer – Encyclopedia of Chem. Tech., Vol. 2, pp. 758–760 (1963).

Kirk – Othmer – Encyclopedia of Chem. Tech., Vol. 21, pp. 112–113 (1970).

Primary Examiner—Leonard Schenkman
Attorney, Agent, or Firm—Howson and Howson

[57] ABSTRACT

An allantoin ascorbic acid complex is disclosed as is an allantoin salt ascorbic acid complex. Medicinal and cosmetic compositions containing these complexes are also disclosed.

1 Claim, No Drawings

TOPICAL COMPOSITIONS CONTAINING AN ALLANTOIN ASCORBIC ACID COMPLEX

This is a divisional of application Ser. No. 462,779, filed Apr. 22, 1974 now U.S. Letters Pat. No. 3,898,243 which issued on Aug. 5, 1975.

BACKGROUND OF THE INVENTION

Allantoin is known to possess soothing, keratolytic moisturizing and anti-irritant properties. Various aluminum salts of allantoin are described in U.S. Pat. No. 2,761,867. These compounds combine the soothing and healing properties of allantoin with the astringent properties of aluminum and have found use in a variety of external cosmetic compositions and internal medicaments. For example, cosmetic chemists have utilized allantoin and allantoin salts in formulating a variety of products such as deodorants, antiperspirants, astringent lotions, after-shave lotions, diaper creams and the like. An alcohol-soluble aluminum chlorhydroxy allantoin propylene glycol complex useful in the formulation of various cosmetic compositions is described in U.S. Pat. No. 3,632,596.

Ascorbic acid (Vitamin C) has found use primarily in the prevention and treatment of scurvy. It has also found use as an antioxidant for fats, oils, aqueous oil emulsions, soft drinks and for the prevention of browning and off-flavors in frozen foods (See Kirk-Othmer, *Encyclopedia of Chemical Technology*, 2nd Edition, Vol. 2, p. 747 et seq. Interscience, 1963). It has also been reported that a one percent solution of ascorbic acid is an effective palliative for pain when applied topically to patients suffering from severe and extensive burns.

Ascorbic acid is quite stable in dry form although it gradually darkens on exposure to light. Solutions of ascorbic acid are sensitive to alkalis and acids. Ascorbic acid is also sensitive to heat; in fact, the viamin is readily oxidized if heated in air. The vitamin is known to deteriorate rapidly in the presence of even traces of metals such as copper and silver and is sensitive to iron and manganese. Despite its widespread use when taken internally for the prevention and treatment of a wide variety of maladies, ascorbic acid has not been utilized in the formulation of cosmetic compositions and topical medicaments because of its sensitivity to light, alkalis, acids, heat and metals and the like.

It is an object of this invention to provide novel compounds containing allantoin or aluminum salts of allantoin and ascorbic acid which are stable both in dry form and solutions and are not sensitive to heat.

It is another object of this invention to provide novel compounds possessing the soothing and healing action of allantoin, the astringent and deodorizing actions of aluminum salts of allantoin and the pain relieving and antioxidant properties of ascorbic acid.

Other objects will become apparent from a consideration of the following specification and claims.

DETAILED DESCRIPTION OF THE INVENTION

The present invention relates to novel complexed compounds of allantoin or aluminum salts of allantoin and ascorbic acid, and, more particularly, to an allantoin ascorbic acid complex; an aluminum chlorhydroxy allantoinate ascorbic acid complex, and an aluminum hydroxy allantoinate ascorbic acid complex.

The novel compounds of the present invention may be depicted as having the formulas:

$[C_4H_5N_4O_3]_x \cdot [C_5H_8O_6]_y$ (allantoin ascorbic acid complex) $[Al_2(OH)_3 ClC_4H_4N_4O_3]_x \cdot [C_5H_7O_6]_y$ (aluminum chlorhydroxy allantoinate ascorbic acid complex) and $[Al(OH)C_2H_4N_4O_3]_x \cdot [C_5H_7O_6]_y$ (aluminum hydroxy allantoinate ascorbic acid complex) wherein x and y are each about 1 and refer to the number of mols of each component. In the foregoing formulas, $C_4H_5N_4O_3$ represents allantoin and $C_5H_8O_6$ represents ascorbic acid.

The novel complexes are prepared by thoroughly mixing the allantoin or the appropriate aluminum salt of allantoin with ascorbic acid in a dry, finely divided state. Hot water, e.g. boiling, distilled water, is then added to the mixture with constant trituration. The resultant mass is then dried to provide the desired complexes. Allantoin, aluminum salts of allantoin and ascorbic acid are available commercially and are used in this form in preparing the complexes described herein.

The relative proportions of allantoin or aluminum salts of allantoin and ascorbic acid utilized in forming the desired complexes may vary somewhat. Regardless of the proportions, however, the products are complex chemical compounds in which the components are chemically bound.

In the complexes of the present invention, the allantoin or aluminum salts of allantoin and the ascorbic acid are preferably combined in a mol ratio of about 1 to 1. Therefore, in the preferred embodiments of this invention allantoin and ascorbic acid are combined in a mol ratio of about 1 to 1 to form the allantoin ascorbic acid complex. Likewise, aluminum chlorhydroxy allantoinate and ascorbic acid are combined in a mol ratio of about 1 to 1 to form the aluminum chlorhydroxy allantoinate ascorbic acid complex while aluminum hydroxy allantoinate and ascorbic acid are combined in a mol ratio of about 1 to 1 to form the aluminum hydroxy allantoinate ascorbic acid complex.

The reaction which occurs on the formation of the desired complexes requires an elevated temperature. Thus, the reaction mixtures are heated to at least 50°C., the upper limit of temperature being dictated by the boiling point of the aqueous medium (100°C.) used in forming the complexes. There is no necessity to supply additional heat to the reaction mixture if, for example, boiling water is added to the mixture of allantoin or aluminum salts of allantoin and ascorbic acid. The amount of water used in the reaction is not critical so long as an amount is added sufficient to wet the intimate mixture of the reactants. Hence, the reaction mixture may take the form of a paste, slurry or a solution. As noted above, the aqueous medium in which the reaction occurs may be water; likewise, a mixture of water and a water-miscible organic liquid like methanol or ethanol, and the like may be utilized.

After the reaction is complete, the water is preferably removed from the product to a level below about 1%, by weight, based on the weight of the complex. This may be accomplished by heating the complex at a temperature of from about 140°F. to about 160°F. until the product is dry and has a relatively constant weight. The dry complexes are white powders. Any drying means including spray drying may be employed, and vacuum may be employed to assist drying.

Despite the well-known instability of ascorbic acid, especially its instability at elevated temperatures, surprisingly it has been found that the complexes produced as the result of the present invention are remarkably stable whether in solution or heated. While not wishing to be bound by any precise theory, it is thought that the amphoteric characteristics of allantoin are responsible for the remarkable stability of the complexed products.

The complexes produced through this invention have the combined attributes of allantoin or the aluminum salts of allantoin e.g. healing, soothing, keratolytic, moisturizing and astringent properties (in the case of aluminum salts), bacteriostatic properties (in the case of aluminum chlorhydroxy allantoinate salts) with the properties of ascorbic acid, e.g. pain relieving, skin nourishing and antioxidant properties. The complexes are thus useful in a myriad of topical preparations such as sunburn preparations, hypoallergenic deodorants, antiperspirants and the like. The complexes also may be incorporated in "sun-tan" or sun-screen compositions and skin bleaching compositions containing hydroquinone such as are described in U.S. Pat. No. 2,376,884 where the ascorbic acid component of the complexes exerts a stabilizing effect through its antioxidant properties. Since the complexes are compatible with halo-carbon propellants, they may be used in aerosol preparations.

The following examples illustrate the properties of typical complexes of the present invention and suggested uses for these complexes. The examples are illustrative only and not intended to limit the scope of the invention.

EXAMPLE 1

158 g. of allantoin are thoroughly mixed with 176 g. of ascorbic acid. 25 to 35 cc. of boiling, distilled water are then added and the mixture is triturated until a uniform wet mass is formed. The resulting complex is then dried for 2 to 3 hours at 150 to 160°F. to a white powder. The product is an allantoin ascorbic acid complex having the formula $[C_4H_5N_4O_3]_x \cdot [C_5H_8O_6]_y$ where x and y are each about 1. A 2% aqueous solution of the complex has a pH of about 4 to about 4.5 and at 25°C. its solubility characteristics are 3 to 5% in water and 20 to 25% in boiling water. The complex may be formulated in pharmaceutically acceptable carriers at levels of from about 0.5 to about 1%, by weight, based on the total weight of the product, to form an agent useful in the treatment of burns and sunburns.

EXAMPLE 2

640 g. of aluminum chlorhydroxy allantoinate are thoroughly mixed with 360 g. of ascorbic acid. 75 to 100 cc. of boiling, distilled water are then added and the mixture is triturated until a uniform wet mass is formed. The resulting complex is then dried for 3 to 4 hours at 140° to 150°F. to a white powder. The product is an aluminum chlorhydroxy allantoinate ascorbic acid complex having the formula:

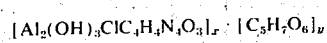

where x and y are each about 1. At 25°C. its solubility characteristics are: 2 to 3% in water; 0.5% in 95% ethanol. The complex may be formulated in pharmaceutically acceptable carriers at levels of from about 0.3 to about 0.5%, by weight, based on the weight of the product, to form a hypoallergenic deodorant.

EXAMPLE 3

700 g. of aluminum hydroxy allantoinate are thoroughly mixed with 300 g. of ascorbic acid. 150 cc. of boiling, distilled water are then added and the mixture is triturated until a uniform wet mass is formed. The resulting complex is then dried for 2 to 3 hours at 150° to 160°F. to a white powder. The product is an aluminum hydroxy allantoinate ascorbic acid complex having the formula:

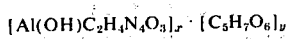

where x and y are each about 1. The complex is insoluble in water. The complex may be formulated in pharmaceutically acceptable carriers at levels of from about 0.3% to 0.5%, by weight, based on the weight of the product, to form diaper rash palliatives and cosmetic preparations.

EXAMPLE 4

The following evaluations were made to demonstrate the usefulness of the allantoin ascorbic acid complex and the aluminum chlorhydroxy allantoinate ascorbic acid complex as a stabilizing agent in cosmetic formulations containing hydroquinone. Each complex was tested in accordance with the procedure described in chapter 6 entitled "Skin Lighteners and Bleach Creams" of the text *Cosmetics: Science and Technology* Vol. 1, 2nd Ed. edited by Balsam and Sagarin (John Wiley & Sons, 1972)

| Hydroquinone Lotion A | |
|---|---|
| Ingredients | % W/W |
| Water | 85.4 |
| Titanium Dioxide | 0.2 |
| Veegum K | 0.5 |
| Cetyl Alcohol | 1.8 |
| Viscolan | 0.6 |
| Glycerin | 5 |
| Giv-Tan F | 1 |
| Cycloryl MS | 1 |
| Allantoin Ascorbic Acid Complex | 0.5 |
| Hydroquinone | 3 |
| Chemoderm 982 | 0.5 |
| Onyxide 500 | 0.05 |

| Hydroquinone Cream A | |
|---|---|
| Ingredients | % W/W |
| Stearic Acid | 14 |
| Cetyl Alcohol | 1.4 |
| Hydroquinone | 3 |
| Allantoin Ascorbic Acid Complex | 0.5 |
| Borax | 0.7 |
| Sodium Carbonate | 1.4 |
| Glycerine | 4 |
| Water | 70.3 |
| Chemoderm 982 | 0.5 |

| Hydroquinone Lotion B | |
|---|---|
| Ingredients | % W/W |
| Water | 84 |
| Titanium Dioxide | 0.2 |
| Veegum K | 0.5 |
| Cetyl Alcohol | 1.8 |
| Glycerin USP | 5 |
| Giv-Tan F | 1.5 |
| Cycloryl MS | 1 |
| Sodium Sulfite | 0.5 |
| Aluminum Chlorhydroxy Allantoinate Ascorbic Acid Complex | 0.5 |
| Citric Acid | 0.5 |
| Hydroquinone | 3 |
| Chemoderm 982 | 0.5 |
| Sodium Bisulfite | 0.4 |

| Hydroquinone Lotion C | |
|---|---|
| Ingredients | % W/W |
| Water | 84 |
| Titanium Dioxide | 0.2 |
| Veegum K | 0.5 |
| Viscolan | 0.6 |

-continued

Hydroquinone Lotion A

| Ingredients | % W/W |
|---|---|
| Glycerin | 5 |
| Giv-Tan F | 1.5 |
| Cycloryl MS | 1 |
| Sodium Sulfite | 0.5 |
| Allantoin Ascorbic Acid Complex | 0.5 |
| Citric Acid | 0.5 |
| Hydroquinone | 3 |
| Chemoderm 982 | 0.5 |
| Sodium Bisulfite | 0.4 |

Hydroquinone Lotion D (Control)

| Ingredients | % W/W |
|---|---|
| Water | 84 |
| Titanium Dioxide | 0.2 |
| Veegum K | 0.5 |
| Viscolan | 0.6 |
| Glycerin | 5 |
| Giv-Tan F | 1.5 |
| Cycloryl MS | 1 |
| Sodium Sulfite | 0.5 |
| Citric Acid | 0.5 |
| Hydroquinone | 3 |
| Chemoderm 982 | 0.5 |
| Sodium Bisulfite | 0.4 |

Samples of each of the foregoing products were filled in both closed and open glass containers. The containers were stored at room temperature (about 25°C.), 45°C. and 90°C. and inspected daily for discoloration indicative of decomposition of the hydroquinone. The formulation containing the allantoin ascorbic acid complex (Hydroquinone Cream A and Hydroquinone Lotion A & C) had better stability under all conditions of storage than did the control (Hydroquinone Lotion D). The formulation containing aluminum chlorhydroxy allantoin ascorbic acid complex exhibited the best stability of all formulations tested. Extrapolating the results of the accelerated aging conditions (i.e. 45°C. and 90°C.) this formulation (Hydroquinone Lotion B) was predicted to remain stable for approximately 2½ years at ambient conditions while the control (Hydroquinone Lotion D) was predicted to remain stable for less than one year at ambient conditions.

Having thus described the invention,

1. A pharmaceutical composition useful for topical application comprising from about 0.5 to about 1%, by weight, based on the weight of the composition, of an allantoin ascorbic acid complex and a pharmaceutically acceptable carrier, said complex being formed by combining allantoin and ascorbic acid in a mol ratio of about 1 to 1.

* * * * *